United States Patent
Lacaille

(10) Patent No.: US 9,816,970 B2
(45) Date of Patent: Nov. 14, 2017

(54) DEVICE FOR DETECTING ANOMALIES IN AN AIRCRAFT TURBINE ENGINE BY ACOUSTIC ANALYSIS

(71) Applicant: SNECMA, Paris (FR)

(72) Inventor: Jérôme Henri Noël Lacaille, Rosny-Sous-Bois (FR)

(73) Assignee: SNECMA, Paris (FR)

( * ) Notice: Subject to any disclaimer, the term of this patent is extended or adjusted under 35 U.S.C. 154(b) by 186 days.

(21) Appl. No.: 14/380,533

(22) PCT Filed: Feb. 22, 2013

(86) PCT No.: PCT/FR2013/050362
§ 371 (c)(1),
(2) Date: Aug. 22, 2014

(87) PCT Pub. No.: WO2013/124591
PCT Pub. Date: Aug. 29, 2013

(65) Prior Publication Data
US 2015/0040650 A1 Feb. 12, 2015

(30) Foreign Application Priority Data
Feb. 24, 2012 (FR) .................................. 12 51713

(51) Int. Cl.
*G01M 15/14* (2006.01)
*G01N 29/44* (2006.01)
(Continued)

(52) U.S. Cl.
CPC .......... *G01N 29/4445* (2013.01); *G01M 7/00* (2013.01); *G01M 15/14* (2013.01); *G01N 29/14* (2013.01); *G07C 5/008* (2013.01); *G07C 5/0808* (2013.01); *G07C 5/0841* (2013.01); *G01H 1/006* (2013.01); *G01N 2291/102* (2013.01); *G01N 2291/2693* (2013.01); *G01N 2291/2694* (2013.01); *G05B 23/0213* (2013.01); *G05B 23/0243* (2013.01)

(58) Field of Classification Search
USPC ......................................... 73/112.01, 112.03
See application file for complete search history.

(56) References Cited

U.S. PATENT DOCUMENTS 6,332,116 B1 * 12/2001 Qian ...................... G01H 1/003
340/683
6,801,873 B1 * 10/2004 Jin .......................... G01P 3/489
702/145

(Continued)

OTHER PUBLICATIONS

International Search Report issued in International Patent Application No. PCT/FR2013/050362, dated May 22, 2013.

*Primary Examiner* — Eric S McCall
(74) *Attorney, Agent, or Firm* — Pillsbury Winthrop Shaw Pittman LLP

(57) ABSTRACT

A device for detecting anomalies in an aircraft turbine engine by acoustic analysis, the device not an onboard device and including: a mobile module including a directional system for acquiring acoustic signals from the turbine engine; a processor for processing the signals, which is suitable for generating a damage report; a transmitter for transmitting the damage report; a server capable of exchanging data with the mobile module, the server including a receiver for receiving the damage report; and a storage device suitable for storing the damage report.

15 Claims, 1 Drawing Sheet

(51) Int. Cl.
  *G01M 7/00*   (2006.01)
  *G01N 29/14*  (2006.01)
  *G07C 5/00*   (2006.01)
  *G07C 5/08*   (2006.01)
  *G01H 1/00*   (2006.01)
  *G05B 23/02*  (2006.01)

(56) References Cited

U.S. PATENT DOCUMENTS

| | | | |
|---|---|---|---|
| 7,363,111 B2 | 4/2008 | Vian et al. | |
| 9,032,785 B1* | 5/2015 | Miles | G01M 15/14 73/112.01 |
| 2002/0033946 A1 | 3/2002 | Thompson | |
| 2003/0066352 A1* | 4/2003 | Leamy | F01D 21/00 73/593 |
| 2007/0261492 A1* | 11/2007 | Board | G01M 13/028 73/587 |
| 2008/0047363 A1* | 2/2008 | Arms | B60C 23/0411 73/862 |
| 2008/0082197 A1* | 4/2008 | Lacaille | G05B 23/0232 700/121 |
| 2010/0101310 A1* | 4/2010 | Perie | G01M 15/042 73/114.25 |
| 2011/0150626 A1* | 6/2011 | Kinzie | G01H 1/003 415/1 |
| 2011/0288836 A1* | 11/2011 | Lacaille | G05B 23/0254 703/2 |
| 2011/0307431 A1* | 12/2011 | Lacaille | G05B 23/0221 706/17 |
| 2013/0197830 A1* | 8/2013 | Dvorak | G06Q 10/20 702/46 |
| 2013/0325286 A1* | 12/2013 | Lacaille | B64F 5/0045 701/99 |
| 2015/0287249 A1* | 10/2015 | Lacaille | G05B 23/0251 701/31.8 |

* cited by examiner

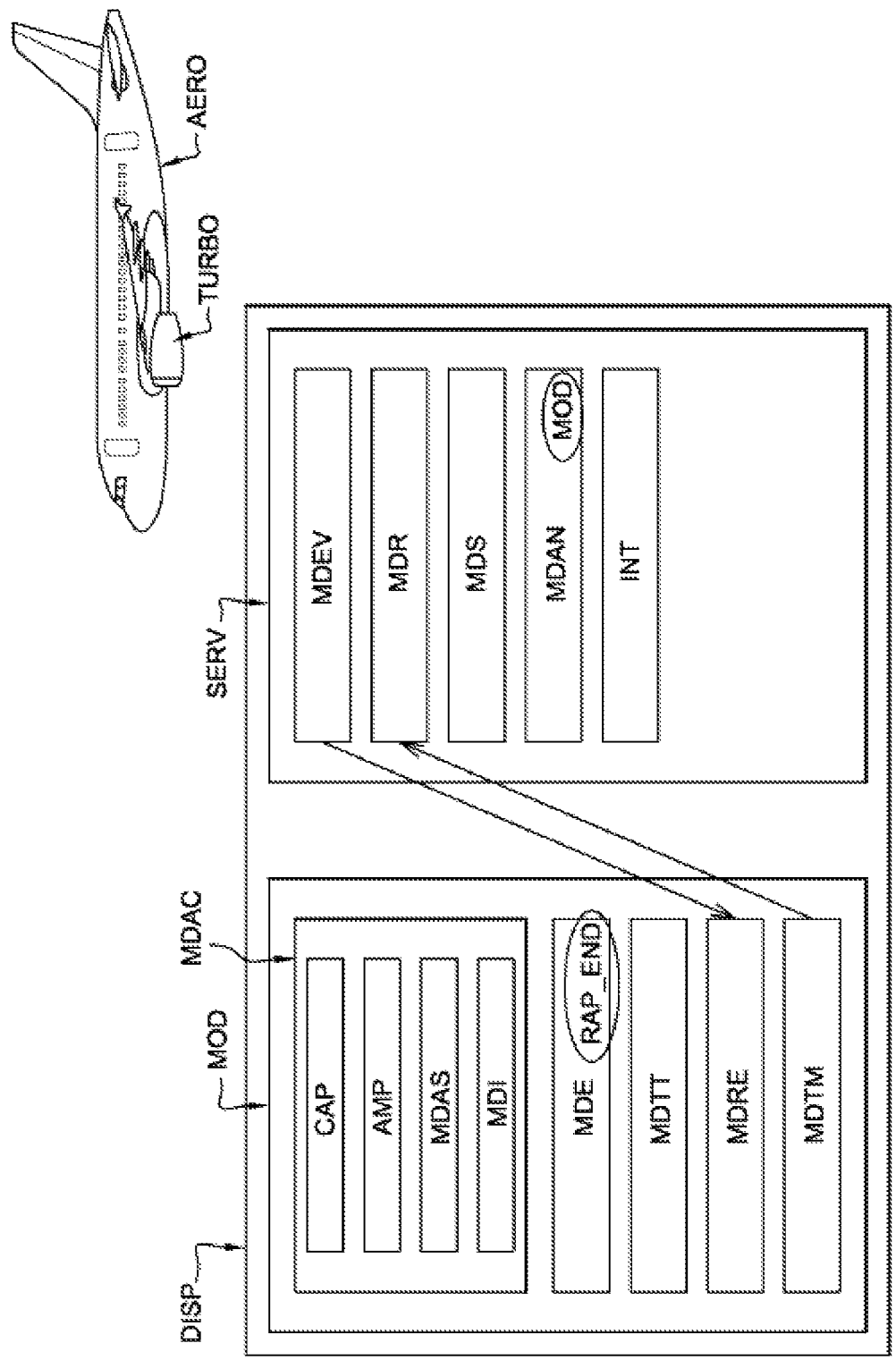

DEVICE FOR DETECTING ANOMALIES IN AN AIRCRAFT TURBINE ENGINE BY ACOUSTIC ANALYSIS

CROSS REFERENCE TO RELATED APPLICATIONS

This application is the U.S. National Stage of PCT/FR2013/050362, filed Feb. 22, 2013, which in turn claims priority to French Patent Application No. 1251713, filed Feb. 24, 2012. The contents of all of these applications are incorporated herein by reference in their entirety.

TECHNICAL FIELD OF THE INVENTION

The technical field of the invention is failure diagnostics of an aircraft turbine engine, and more particularly failure diagnostics by acoustic analysis or vibrational analysis. This invention relates to a device for detecting anomalies of an aircraft turbine engine by acoustic analysis.

TECHNOLOGICAL BACKGROUND OF THE INVENTION

Failures that occur in rotating machines such as aircraft turbine engines can rarely be detected visually, or when they can be detected it is too late to take action. Consequently, diagnostic methods are necessary to predict failures and minimise their consequences. An attempt is thus made to anticipate part failures that could damage the machine or could leave a fragment of a broken part in the machine.

The acoustic analysis is the most frequently used among all the different physical phenomena used to demonstrate functional defects or degradation of a rotating machine. Vibrations are characteristic of the condition of the equipment, and the terms vibration signature and acoustic signature are used. Sampling and processing of the vibration signature can quickly give information about the condition of the equipment and the variation with time can be monitored without needing to disassemble the machine.

There are many engine problems that can occur in a turbine engine and can be identified from vibrations, for example rotor-stator contacts, ingress of foreign bodies, abnormal unbalanced mass, bearing defect (chipped balls or rings), gear engagement defects (worn or damaged teeth), defective auxiliary system (pump, etc.).

Before an acoustic analysis of a turbine machine can be performed, data have to be acquired over a relatively long period which makes it difficult to transfer data from the aircraft to the ground. Furthermore, it is difficult to envisage processing these data directly onboard the aircraft because such processing requires a high calculation power. This means that simplified measurements have to be made in order to detect obvious abnormal phenomena such as an out-of-balance mass or large ingested foreign bodies.

Therefore data are conventionally retrieved and analysed on the ground on a test bench, said test bench being provided with high frequency acquisition systems and powerful computers. Mechanical phenomena are easier to detect during transient phases. However, the disadvantage is that the turbine engine has to be disassembled.

GENERAL DESCRIPTION OF THE INVENTION

The purpose of the invention is a device and method of detecting anomalies by acoustic analysis of an aircraft turbine engine that does not require the engine to be disassembled nor processing of data onboard the aircraft nor transmission of data from the aircraft to the ground.

According to a first aspect, the invention essentially concerns a device for detection of anomalies by acoustic analysis of an aircraft turbine engine, characterised in that it is not onboard and that it comprises:
  at least one mobile module comprising:
    directional acquisition means to acquire acoustic signals from the turbine machine;
    means of processing said signals, adapted to generate a damage report;
    means of transmitting said damage report;
  a server capable of exchanging data with the at least one module, said server comprising:
    means of reception of the damage report;
    storage means adapted to store said damage report.

With the device according to the invention, the acoustic signals are retrieved by the non-embarked mobile module directly from the ground, when the aircraft is parked (for start-up and stop tests of the turbine machine) or when the aircraft is taking off or landing, using directional acquisition means capable of adapting as a function of movements of the aircraft. Signals are then processed by processing means, advantageously computers with a high calculation power that is not available onboard the aircraft. A damage report is finally sent to the server that stores it, said server advantageously being capable of receiving search reports from different modules.

Apart from the main characteristics mentioned in the above paragraph, the device according to the invention may have one or several complementary characteristics among the following, considered individually or in any technically possible combination:
  the acquisition means comprise a directional sensor such as a microphone, and a parabolic amplifier,
  the acquisition means comprise slaving means adapted to control the orientation of the directional sensor,
  when the aircraft is moving, the slaving means adjust the orientation of the sensor depending on the position and trajectory of the aircraft,
  the acquisition means comprise aircraft identification means,
  each module comprises means of recording acoustic signals acquired using the acquisition means,
  the server comprises a user interface adapted to enable a user to display a damage report
  the server reception means are adapted to receive data from the aircraft,
  the server comprises analysis means capable of using data from the aircraft.

According to a second aspect, the invention relates to a method of detecting anomalies by acoustic analysis of an aircraft turbine engine, said method being implemented by a device according to any one of the previous claims, said method comprising successive steps for:
  acquisition of acoustic signals from the turbine engine;
  processing of said signals so as to generate a damage report;
  transmission of said damage report to the server;
  storage of said damage report.

The invention and its different applications will be better understood after reading the following description and an examination of the accompanying FIGURES.

BRIEF DESCRIPTION OF THE FIGURE

The FIGURE is only shown for information and is in no way limitative of the invention.

The FIGURE shows a block diagram representing modules making up a device according to one embodiment of the invention.

DETAILED DESCRIPTION OF AT LEAST ONE EMBODIMENT OF THE INVENTION

The FIGURE diagrammatically shows a device DISP for detection of anomalies by acoustic analysis of a turbine machine TURBO of an aircraft AERO according to one embodiment of the invention. Said device DISP is not onboard the aircraft AERO and is used for acoustic analyses when the aircraft AERO is in the takeoff or landing phase, or is parked.

The device DISP comprises:
- a mobile module MOD comprising:
    - acquisition means MDAC for acquiring acoustic signals SIG, said acquisition means MDAC comprising:
        - a directional microphone CAP;
        - a parabolic amplifier AMP;
        - slaving means MDAS;
        - identification means MDI to identify the aircraft AERO;
    - means MDE for recording acoustic signals SIG;
    - means MDTT for processing acoustic signals SIG;
    - transmission means MDTM;
    - retrieval means MDRE; and
- a remote server SERV comprising:
    - reception means MDR;
    - storage means MDS;
    - analysis means MDAN;
    - transmission means MDEV;
    - a user interface INT.

The main functions of the module MOD are acquisition of acoustic signals SIG originating from the turbine machine TURBO through acquisition means MDAC, and processing of these signals through recording means MDE and processing means MDTT. The transmission means MDTM of the module MOD and reception means MDR of the server SERV are adapted to communicate with each other. Thus, the server SERV can receive data from the module MOD. The main functions of the server SERV are storage of said data through storage means MDS and viewing of these data through the user interface INT. Note that in one embodiment, the interface INT is physically separate from other components of the server SERV. In one embodiment of the invention, the device DISP comprises two modules MOD, the server is then capable of communicating with each module MOD. Two modules MOD can simultaneously analyse the two engines of the aircraft AERO.

It would also be possible for the server SERV to be shared by several mobile modules MOD. Thus the server SERV receives data from several modules MOD analysing turbine engines TURBO on different aircraft AERO, and said data can then be viewed centrally from the user interface INT of the server SERV.

The identification means MDI are used to identify the aircraft AERO in the case in which the server SERV is shared with several modules MOD. In one embodiment, the identification means MDI are view taking means. The view taking means MDI trip at a determined sound energy detection threshold so that a photograph of the aircraft AERO can be taken and used to identify the aircraft AERO by means of recognition algorithms well known to those skilled in the art, so that the aircraft name can be recognised. In another embodiment, the identification means MDI comprise a user interface installed on the module MOD by which a user inputs the name of the aircraft AERO for which the turbine machine TURBO is analysed. Note that this interface can also be used to adjust the orientation of the microphone CAP, possibly with display for assistance in monitoring or to check tracking parameters or to adjust other algorithmic pre-processing parameters.

In another embodiment, the identification means MDI are sensors capable of capturing radio emissions from the aircraft AERO or the airport, said emissions possibly containing information about the aircraft AERO. Finally in another embodiment, the identification means MDI use means provided by the airport such as take off/landing schedules to help identify the aircraft AERO. The identification means MDI can advantageously save the analysis date and time, and possibly other observations such as the location.

Due to the mobility of the module MOD, the module can be brought close to a turbine machine TURBO of the aircraft AERO to be analysed without needing to remove the turbine engine TURBO and put it on a test bench. If the aircraft AERO is immobile, an operator orients the microphone CAP manually to face the turbine engine TURBO, or the microphone CAP will automatically orient itself along a direction at which it picks up maximum sound emissions.

When the aircraft AERO is moving, in other words during the take off and landing phases, the slaving means MDAS adapt the orientation of the directional microphone CAP such that it follows the trajectory of the aircraft AERO to optimally capture the acoustic signals SIG. In one embodiment, the microphone CAP is fixed to a mobile axis slaved by slaving means MDAS operating by means of scanning and tracking algorithms known to those skilled in the art. The following describes some example publications describing scanning and tracking algorithms:

J. Lacaille, "Industrialisation d'algorithmes mathématiques" (Industrialisation of mathematical algorithms), Paris 1, 2004

J.-Francois Boulanger, F. Galland, P. Réfrégier, and P. Martin, "Détection et poursuite de cibles par minimisation de la complexity stochastique" (Detection and tracking of targets by minimisation of stochastic complexity), in *MajecSTIC*, 2009, pp. 1-4.

S. Kumar, "Detection and Tracking Algorithms for IRST," Bombay, 2004.

W. Hao, C. Sankaranarayanan, Aswin, and R. Chellappa, "Online Empirical Evaluation of Tracking Algorithms," *Applied Physics*, pp. 1-37, 2009.

M. Lashley, "Kalman Filter Based Tracking Algorithms For Software GPS Receivers," Auburn University, 2006.

Slaving means MDAS operate in two steps:
- In a first step called the scanning step, the orientation of the axis quickly scans a sector in space by rotation of the axis, so that the microphone CAP detects a zone that is the source of a loud sound emission. This zone is called the hot point.
- In a second step called the tracking step, the hot point (moving) is detected again and several times, the slaving means MDAS making a fast adjustment of the orientation of the microphone CAP around the first detections. Successive coordinates of the hot point are saved using the cylindrical coordinates of the axis. This sequence of positions is used to estimate a three-part local trajectory (position, speed, acceleration) of the aircraft AERO. The slaving means MDAS thus progressively orient the microphone CAP by applying an estimated direction in anticipation, while continuing to make small random local adjustments in order to refine the position of the hot point with time. The estimated trajectory thus becomes more and more precise.

The microphone CAP is associated with the parabolic amplifier AMP that amplifies sound emissions captured by the microphone CAP. When the quality of the detected acoustic signal SIG is sufficient, recording lasting a few seconds is made using the recording means MDE. This recording is then processed by the processing means MDTT. The processing means MDTT are used to generate reports called "damage reports" RAP-END, listing failures detected in the analysed turbine engine TURBO. The processing means MDTT include processing algorithms, two examples of which are given below.

The first algorithm is described in documents:
"Environment for processing of wideband signal", E. Rudyk, R. Klein, RDK, PHM 2009;
"Environment for vibration based diagnostics", R. Klein, RDK, PHM 2010.

This algorithm requires an identification of the type of the turbine engine TURBO using the identification of the aircraft AERO by the identification means MDI. The algorithm can identify very specific anomalies on bearings or gears provided that the characteristics of the analysed turbine engine TURBO are well known.

The second algorithm is described in the document "Identification of independent vibration sources", A. Hazan, SAMM, University of Paris 1 Pantheon Sorbonne. This algorithm is more general than the first algorithm but it does require that the algorithm should create a learnt model MODEL determined as a function of successive sound spectra of the analysed turbine machine TURBO. Therefore, the algorithm is not capable of detecting an anomaly during the first recordings, but only after a database of spectra associated with the turbine machine TURBO has been created, and after an increasingly sophisticated model MODEL has been created.

The module MOD receives the models MODEL used by the second algorithm through retrieval means MDRE, the models originate from the server SERV that sent them through said transmission means MDEV. The server SERV creates said models MODEL from the engine shaft rotation speeds of the turbine machine TURBO being analysed. Said speeds can easily be identified by an order tracking algorithm, an example of which is given in the document "Trajectory clustering for vibration detection in aircraft engines", A. Hazan, ICDM 2010. Such an algorithm detects anomalies or abnormal trends that are immediately transferred to the server SERV in the form of a detection report by a transmission system such as Wifi or 3G.

The analysis means MDAN of the server SERV create models MODEL from the detection reports, and the server SERV sends them to the module MOD. It should be noted that in one preferred embodiment, users can view the models MODEL through a Web interface to which users can subscribe. Each user can only display data related to aircraft AERO for which he has rights, but the server SERV can use detection reports related to several aircraft AERO to create sophisticated models MODEL specific to a particular type of aircraft AERO or a type of turbine engine TURBO. Thus, if a model MODEL specific to a turbine engine TURBO is not available, it will still be possible to use models MODEL based on a similar type of turbine engine TURBO. Clients can thus subscribe to an additional service informing them about the creation of new models MODEL concerning them.

Starting from models MODEL, the second algorithm calculates a breakdown of the logarithm of an average spectrum into wavelets. The coefficients of this breakdown are used as indicators for the detection of anomalies and creation of a damage report RAP-END.

Regardless of whether the first algorithm or the second algorithm or other algorithms not described is or are used, the processing means MDTT finally create a damage report RAP_END. Said damage reports RAP_END are then transmitted from the module MOD to the server SERV that stores them through storage means MDS. Damage reports RAP_END can be viewed from the user interface INT of the server SERV or by remote connection of users from another interface through an Internet protocol. Users subscribed to the service receive damage reports RAP_END automatically or on request.

The invention claimed is:

1. A device for detecting anomalies by acoustic analysis of an aircraft turbine engine, the device comprising:
   at least one mobile module that is movable relative to the aircraft turbine engine to acquire acoustic signals from the aircraft turbine engine, the at least one mobile module comprising:
      directional acquisition means to acquire the acoustic signals from the turbine engine;
      means of processing said signals, adapted to generate a damage report;
      means of transmitting said damage report;
   a server capable of exchanging data with the at least one module, said server comprising:
      means of reception of the damage report;
      storage means adapted to store said damage report,
   wherein the anomalies are detectable by said device without providing said device onboard the aircraft,
   wherein the directional acquisition means include a directional sensor and slaving means, the slaving means configured to move the directional sensor relative to the aircraft based on a position of the aircraft.

2. The device according to claim 1, wherein the acquisition means comprise aircraft identification means.

3. The device according to claim 1, wherein the at least one module comprises means of recording acoustic signals acquired using the acquisition means.

4. The device according claim 1, wherein the server comprises a user interface adapted to enable a user to display a damage report.

5. A method of detecting anomalies by acoustic analysis of an aircraft turbine engine, said method being implemented by a device according to claim 1, said method comprising:
   acquiring acoustic signals from the turbine engine;
   processing said signals so as to generate a damage report;
   transmitting said damage report to the server;
   storing said damage report.

6. The device according to claim 1, wherein the reception means of the server are adapted to receive data from the aircraft.

7. The device according to claim 6, wherein the server comprises analysis means capable of using data from the aircraft.

8. A device for detecting anomalies by acoustic analysis of an aircraft turbine engine, the device comprising:
   at least one mobile module comprising:
      directional acquisition means to acquire acoustic signals from the turbine engine;
      means of processing said signals, adapted to generate a damage report;
      means of transmitting said damage report;

a server capable of exchanging data with the at least one module, said server comprising:
  means of reception of the damage report;
  storage means adapted to store said damage report,
    wherein the anomalies are detectable by said device without providing said device onboard the aircraft, and
    wherein the acquisition means comprise a directional sensor, and a parabolic amplifier.

9. The device according to claim 8, wherein the directional sensor is a microphone.

10. The device according to claim 8, wherein the acquisition means comprise slaving means adapted to control the orientation of the directional sensor.

11. The device according to claim 10, wherein, when the aircraft is moving, the slaving means adjust the orientation of the sensor depending on the position and trajectory of the aircraft.

12. A device for detecting anomalies by acoustic analysis of an aircraft turbine engine, the device comprising:
  a mobile module comprising:
    a directional acquisition system constructed and arranged to acquire acoustic signals from the turbine engine, the directional acquisition system including a directional sensor configured to detect the acoustic signals and an amplifier configured to amplify the detected acoustic signals;
    a processor constructed and arranged to process said amplified detected acoustic signals, and to generate a damage report;
    a transmitter constructed and arranged to transmit said damage report;
  a server constructed and arranged to exchange data with the mobile module, said server comprising:
    a receiver constructed and arranged to receive the damage report;
    a storage device constructed and arranged to store said damage report,
    wherein the anomalies are detectable by said device without providing said device onboard the aircraft, and
    wherein the directional acquisition system includes an identification system comprising a camera to identify the aircraft.

13. The device according to claim 12, wherein the directional sensor is a microphone.

14. A device for detecting anomalies by acoustic analysis of an aircraft turbine engine, the device comprising:
  a mobile module comprising:
    a directional acquisition system constructed and arranged to acquire acoustic signals from the turbine engine, the directional acquisition system including a directional sensor configured to detect the acoustic signals and an amplifier configured to amplify the detected acoustic signals;
    a processor constructed and arranged to process said amplified detected acoustic signals, and to generate a damage report;
    a transmitter constructed and arranged to transmit said damage report;
  a server constructed and arranged to exchange data with the mobile module, said server comprising:
    a receiver constructed and arranged to receive the damage report;
    a storage device constructed and arranged to store said damage report,
  wherein the anomalies are detectable by said device without providing said device onboard the aircraft, and
  wherein the directional sensor is movable to follow a trajectory of the aircraft.

15. The device according to claim 14, wherein the directional sensor is a microphone.

* * * * *